United States Patent
Lutz

(10) Patent No.: US 9,926,575 B2
(45) Date of Patent: Mar. 27, 2018

(54) METHOD FOR OPERATING A BIOREACTOR THAT METHANIZES BIOMASS

(71) Applicant: BEKON GmbH, Marienfeld (DE)

(72) Inventor: Peter Lutz, Munich (DE)

(73) Assignee: BEKON GmbH, Marienfeld (DE)

( * ) Notice: Subject to any disclaimer, the term of this patent is extended or adjusted under 35 U.S.C. 154(b) by 551 days.

(21) Appl. No.: 14/474,120

(22) Filed: Aug. 30, 2014

(65) Prior Publication Data

US 2015/0068259 A1 Mar. 12, 2015

Related U.S. Application Data

(63) Continuation-in-part of application No. PCT/EP2013/054339, filed on Mar. 5, 2013.

(30) Foreign Application Priority Data

Mar. 6, 2012 (DE) .................... 20 2012 100 788 U
Mar. 7, 2012 (DE) .................... 20 2012 100 816 U

(51) Int. Cl.
C05F 11/00 (2006.01)
C12P 5/02 (2006.01)
(Continued)

(52) U.S. Cl.
CPC .............. *C12P 5/023* (2013.01); *C05F 11/00* (2013.01); *C12M 21/04* (2013.01); *C12M 21/16* (2013.01);
(Continued)

(58) Field of Classification Search
CPC . C05F 17/0217; C05F 17/0229; C12M 21/04; C12M 21/16
See application file for complete search history.

(56) References Cited

U.S. PATENT DOCUMENTS 4,356,269 A * 10/1982 Thomsen .................. C02F 3/28
                                                     210/180
7,211,429 B1   5/2007 Rudas ........................... 435/262
(Continued)

FOREIGN PATENT DOCUMENTS

CN       101258234 A    3/2008
CN       101326278 A    6/2008
(Continued)

OTHER PUBLICATIONS

Fowles et al., "Demonstration of a double-ended in-vessel composting system". Envar LTD, Feb. 19, 2010, pp. 60-67.*
(Continued)

*Primary Examiner* — William H. Beisner
(74) *Attorney, Agent, or Firm* — Imperium Patent Works; Darien K. Wallace

(57) ABSTRACT

The invention relates to a bioreactor for methanizing biomass, a biogas plant having a plurality of such bioreactors, and a method for operating such a bioreactor. Because the elongated reactor vessel includes both a loading gate and an unloading gate that are arranged at opposite ends of the elongated reactor vessel, it is possible to remove consumed biomass, which is harmless in terms of epidemiologic hygiene and plant hygiene due to thermophilic process control during the fermentation, from the reactor vessel through the unloading gate and to transfer this consumed biomass directly to the composting process. The bioreactor thus has a "clean" unloading gate and an "unclean" loading gate.

12 Claims, 3 Drawing Sheets

(51) Int. Cl.
*C12M 1/107* (2006.01)
*C12M 1/16* (2006.01)
*C12M 1/26* (2006.01)
*C12M 1/12* (2006.01)

(52) U.S. Cl.
CPC ............ *C12M 33/00* (2013.01); *C12M 37/04* (2013.01); *Y02E 50/343* (2013.01); *Y02P 20/145* (2015.11); *Y02W 30/47* (2015.05)

(56) References Cited

U.S. PATENT DOCUMENTS

| | | | |
|---|---|---|---|
| 8,053,228 B2 | 11/2011 | Lutz | 435/290.1 |
| 8,105,823 B2 | 1/2012 | Lutz | 435/300.1 |
| 2009/0155892 A1* | 6/2009 | Lutz | C12M 21/04 435/289.1 |
| 2009/0239209 A1* | 9/2009 | Lutz | C05F 17/0027 435/3 |

FOREIGN PATENT DOCUMENTS

| | | |
|---|---|---|
| DE | 3830289 | 9/1988 |
| DE | 20318783 U1 | 12/2003 |
| DE | 202005019132 U1 | 12/2005 |
| DE | 202005019132 U1 | 12/2005 |
| DE | 102007025903 | 6/2007 |
| DE | 102008015240 | 3/2008 |
| DE | 102010024639 | 6/2010 |
| EP | 1301583 | 7/2001 |
| GB | 1009551 | 8/1961 |
| WO | WO 2002/006439 | 7/2001 |
| WO | WO 2005/054423 | 12/2004 |
| WO | WO 2005/054423 A2 | 12/2004 |
| WO | WO 2005/085411 A2 | 3/2005 |
| WO | WO 2007/028642 | 9/2006 |
| WO | WO 2007/028642 A1 | 9/2006 |
| WO | WO 2007/065688 | 12/2006 |

OTHER PUBLICATIONS

Search report dated Oct. 16, 2012, from the German Patent Office in the related foreign application DE202012100816.5 (5 pages).
Office action dated Mar. 24, 2016, from the Chinese Patent Office in the related foreign application CN201380010227.8 (6 pages).
English translation of Office action dated Mar. 24, 2016, from the Chinese Patent Office in the related foreign application CN201380010227.8 (9 pages).
Office action dated Jul. 22, 2015, from the Chinese Patent Office in the related foreign application CN201380010227.8 (7 pages).
English translation of Office action dated Jul. 22, 2015, from the Chinese Patent Office in the related foreign application CN201380010227.8 (10 pages).

* cited by examiner

METHOD FOR OPERATING A BIOREACTOR THAT METHANIZES BIOMASS

CROSS REFERENCE TO RELATED APPLICATION

This application is filed under 35 U.S.C. § 111(a) and is based on and hereby claims priority under 35 U.S.C. § 120 and § 365(c) from International Application No. PCT/EP2013/054339, filed on Mar. 5, 2013, and published as WO 2013/131876 A1 on Sep. 12, 2013, which in turn claims priority from German Application No. 202012100788.6, filed in Germany on Mar. 6, 2012, and from German Application No. 202012100816.5, filed in Germany on Mar. 7, 2012. This application is a continuation-in-part of International Application No. PCT/EP2013/054339, which is a continuation-in-part of German Application Nos. 202012100788.6 and 202012100816.5. International Application No. PCT/EP2013/054339 is pending as of the filing date of this application, and the United States is an elected state in International Application No. PCT/EP2013/054339. This application claims the benefit under 35 U.S.C. § 119 from German Application Nos. 202012100788.6 and 202012100816.5. The disclosure of each of the foregoing documents is incorporated herein by reference.

TECHNICAL FIELD

The present invention relates to a bioreactor for methanizing biomass, a biogas plant with a plurality of such bioreactors, and a method for operating such a bioreactor.

BACKGROUND

A bioreactor of the type presented here is known from European Patent EP1301583 B1 to the present applicant. The complete contents of the disclosure of EP 1301583 B1 with regard to the constructive design is incorporated herein by reference. This known bioreactor is constructed in the manner of a prefabricated garage and has a front and a back end. The complete front end is open and is closed by a flap-shaped gate in an airtight manner. Fresh biomass can be introduced through the gate into the bioreactor and used biomass discharged from the bioreactor through it. The used or spent biomass is composted in a customary manner. According to the governing German biowaste regulations (BioabfV), compost may be discharged on open spaces and green areas only if the biowaste is harmless with regard to diseases and phytohygiene. For example, weed seeds and phytopathogenic germs, such as fire blight pathogens, must be killed. In order to kill diseases, weed seeds and phytopathogenic germs, the temperature in the composted matter must be maintained at a certain temperature range for a given time. This increases the requirements on the care that must be taken during the composting. If biogas is already produced in a thermophilic range (temperature >55° C.), then less care must be taken during the subsequent composting of the spent biomass. However, there is the danger in the bioreactors known from EP1301583 B1 that the spent biomass will be re-contaminated as the bioreactor is discharged, and the spent biomass will have to be decontaminated before it is composted.

Starting from the bioreactor according to EP1301583 B1, the present invention has the objective of designing a bioreactor in which the danger of contamination of the spent biomass with regard to diseases and phytohygiene is considerably reduced. Furthermore, the invention has the objective of providing a method for operating such a bioreactor.

SUMMARY

A bioreactor that generates methane through dry fermentation of biomass includes an elongated reactor container, a biogas removal outlet, a loading gate and an unloading gate. The reactor container has a bottom plate, a cover plate, two side walls, a front end and a back end. The reactor container is made of steel-reinforced concrete and has a rectangular cross section. The biomass rests on the bottom plate between a first retention device and a second retention device. The bottom plate is flush with the ground allowing biomass to be pushed by a loader bucket across the ground, through the front end and onto the bottom plate. The methane exits the reactor container through the biogas removal outlet. The loading gate seals the front end in an airtight manner when the loading gate is closed, and the unloading gate seals the back end in an airtight manner when the unloading gate is closed. The loading and unloading gates cover substantially all of the cross-sectional area of the reactor container at the front and back ends, respectively. The gates are constructed as flaps that articulate from the top of the reactor container.

The first retention device is disposed inside the reactor container adjacent to the loading gate, and the second retention device is disposed inside the reactor container adjacent to the unloading gate. The first retention device prevents the biomass from pressing against the loading gate, and the second retention device prevents the biomass from pressing against the unloading gate. A first percolate drainage system is disposed between the first retention device and the closed loading gate, and a second percolate drainage system is disposed between the second retention device and the closed unloading gate. Percolate that seeps out of the biomass during fermentation is collected using the percolate drainage systems.

A method of operating a bioreactor that methanizes biomass involves loading a reactor container, sealing the ends of the container, generating methane and unloading the spent biomass. The bioreactor has a reactor container that includes a bottom plate, a cover plate, two side walls, a front end and a back end. The reactor container is made of steel-reinforced concrete and has a rectangular cross section. The reactor container is loaded with unfermented biomass only through a loading gate at the front end of the container. The biomass rests on the bottom plate. The loading of the reactor container is performed by pushing unfermented biomass in a loader bucket through the front end and onto the bottom plate that is flush with the ground. The biomass is prevented from pressing against the unloading gate by pushing the biomass against a retention device disposed inside the reactor container adjacent to the unloading gate.

The front end of the reactor container is sealed in an airtight manner by closing the loading gate. Methane is generated by fermenting the biomass using dry fermentation within a temperature range of 50° C. to 60° C. The spent biomass is unloaded from the reactor container only through an unloading gate at the back end of the reactor container. A retention device that retains the biomass is removed after the unloading gate is opened but before the spent biomass is unloaded from the reactor container. The unloading gate seals the back end in an airtight manner when the unloading gate is closed. The unloading gate covers substantially all of the cross-sectional area of the reactor container at the back end when the unloading gate is closed. The unloading gate is constructed as a flap that articulates from the top of the reactor container.

The spent biomass is composted directly after unloading the spent biomass from the reactor container without first decontaminating the spent biomass after the spent biomass has been unloaded from the reactor container. The loading, sealing and unloading is repeated so as to generate methane in multiple batch operations. The generated methane is supplied to a cogeneration unit.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 1:
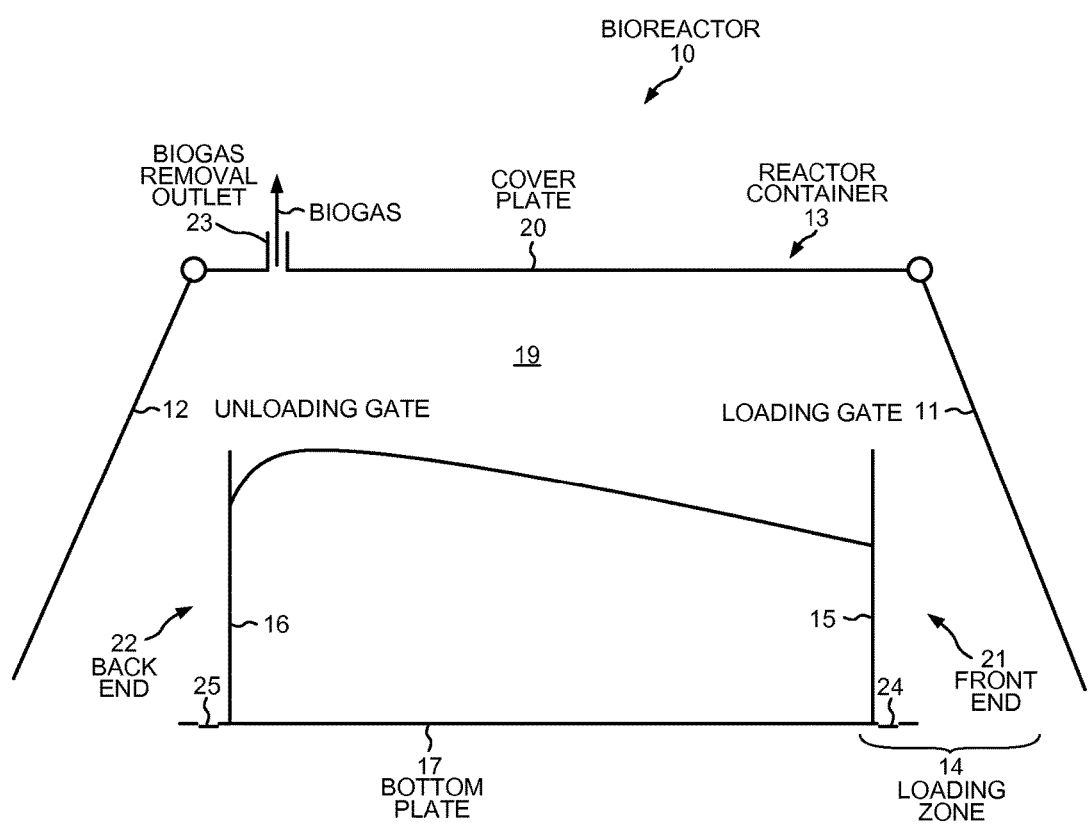
FIG. 1 is a schematic, vertical cross-sectional view of a bioreactor with two gates in accordance with the invention.

FIG. 1 is a schematic, cross-sectional view of a bioreactor 10 according to the present invention. The bioreactor 10 has a loading gate 11 and an unloading gate 12 arranged at opposite ends of an elongated reactor container 13. Elongated reactor container 13 has a rectangular cross section and is more than twice as long as the container ends are wide. Fresh and thus contaminated biomass is loaded into the reactor container 13 through the loading gate 11. The bioreactor 10 generates methane from biomass using dry fermentation. Dry fermentation allows biomass from organic wastes, agricultural waster and communal garden and park areas to be methanized without transforming the materials into a pumpable, liquid substrate. It is possible to ferment biomasses having a dry substance fraction of up to 50%. The spent and thus thermally processed biomass is discharged from the reactor container 13 through the unloading gate 12 at the opposite end of the container 13. The thermal or thermophilic processing during the digestion renders the spent biomass harmless with regard to diseases and phytohygiene. The subsequent composting is less troublesome as regards diseases and phytohygiene. Therefore, the bioreactor has a "clean" unloading gate 12 and an "unclean" loading gate 11. The "clean" unloading gate 12 is exclusively used to discharge or unload spent and "clean" biomass from the reactor container 13. The "unclean" loading gate 11 at the opposite end of the reactor container 13 is exclusively used to load unfermented, fresh and therefore hygienically contaminated biomass into the reactor container 13. The length of the reactor container puts a significant distance between the "clean" unloading gate 12 and the "unclean" loading gate 11. Therefore, it is less likely that the spent biomass will be re-contaminated as it is unloaded from the reactor container 13. Undesired germs, seeds and bacteria from the area 14 around the loading gate 11 thus cannot pass into the "clean" area of the unloading gate 12. It is possible by means of the bioreactor with two gates to spatially separate a "clean", i.e., harmless with regard to diseases and phytohygiene, discharge zone from the loading zone 14, which is not harmless with regard to diseases and phytohygiene.

In thermophilic processing during the generation of biogas, including methane, the generation of biogas takes place with bacteria that optimally "work" in a temperature range of approximately 50° C. to 60° C. In mesophilic processing, however, the generation of biogas is performed by bacteria strains that optimally "work" in the range of approximately 30° C. and 35° C. Therefore, in the thermophilic processing during the generation of biogas, the spent biomass is already rendered harmless with regard to diseases and phytohygiene, and the directly following composting can be carried out with less supervision and care.

The loading and unloading of the reactor container 13 is facilitated by the passable floor of the reactor container that is flush with the ground allowing the use of front-end loader buckets on both wheeled and tracked loading devices, such as tractors and caterpillars. To facilitate access of such wheeled or tracked loading devices, the two gates on opposite ends of the reactor container 13 open nearly the entire cross section of the reactor container. Thus, loading gate 11 covers substantially all of the cross-sectional area of reactor container 13 at the front end, and unloading gate 12 covers substantially all of the cross-sectional area of reactor container 13 at the back end. Because the floor of reactor container 13 is flush with the ground, biomass can be pushed by a loader bucket across the ground, through the front end and onto the bottom plate. Similarly, spent biomass can easily be removed from the reactor container 13 by pushing the spent biomass across the floor and out the back end. By constructing the reactor containers in a manner similar to prefabricated garage modules, the production costs for the reactor container are reduced.

Loading and unloading the reactor container 13 is facilitated by constructing the gates 11-12 as flaps so as to make both ends of the reactor container fully removable through hydraulic actuation of the two gates. Retention devices 15-16 are used inside the reactor container 13 to prevent the biomass from contacting the closed gates 11-12. The retention devices 15-16 prevent excessive pressure from the expanding biomass from pressing against the gates. Accordingly, the gates can be constructed from lighter material and are less costly. The quasi-continuous generation of biogas in multiple batch operations is possible by using a plurality of biogas reactor containers in a biogas plant.

The biogas reactor or bioreactor 10 of FIG. 1 is made of steel-reinforced concrete or of ashlar-formed masonry blocks. The bioreactor 10 can be constructed in the manner of a prefabricated garage. The longitudinally extending reactor container 13 includes four planar concrete elements, namely, a bottom plate 17, two side walls 18 and 19, a cover plate 20 and an open front end 21, an open back end 22 and a biogas removal connection 23. The open front end 21 can be closed airtight by the loading gate 11, and the open back end 22 can be closed airtight by the unloading gate 12. Both gates 11-12 can be opened and closed hydraulically. Each of the gates 11-12 is constructed as a flap that articulates from the top of the reactor container 13. For additional details regarding the design of a hydraulically actuated gate of a bioreactor, see U.S. Pat. No. 8,053,228 dated Nov. 8, 2011, entitled "Bioreactor Comprising a Retaining System," which is incorporated herein by reference.

Figure 2:
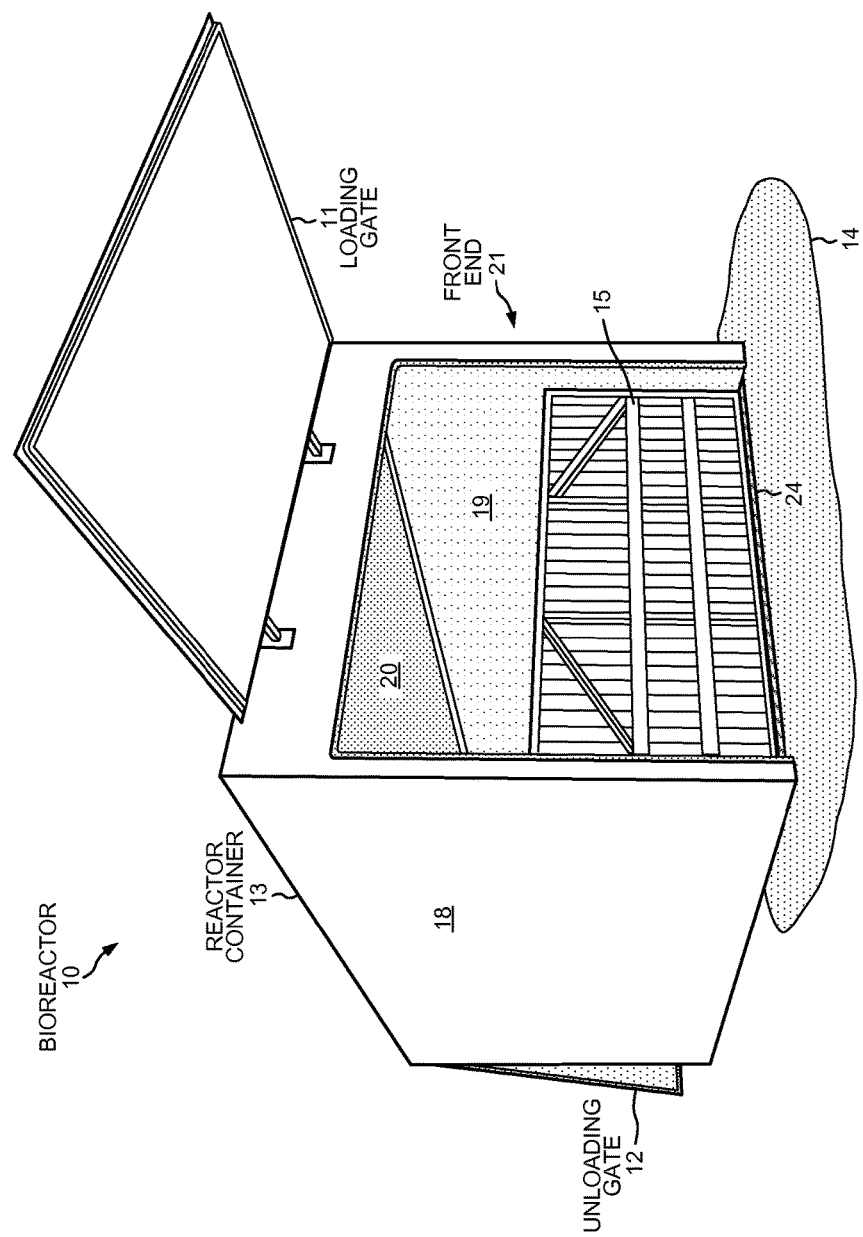
FIG. 2 shows a perspective view of the bioreactor of FIG. 1 from the front with an open loading gate.

FIG. 2 shows a perspective view of the front end 21 of the reactor container 13 with open loading gate 11. A first retention device 15 in the form of a vertical wall element is provided in the reactor container 13 directly behind the loading gate 11. In order to load the reactor container 13 with fresh biomass, the first retention device 15 is first removed. The biomass is then pushed up against a second retention device 16 provided adjacent to the unloading gate 12 at the back end of the reactor container 13. Then the first retention device 15 is mounted into the reactor container 13 prior to closing the loading gate 11. The first retention device 15 prevents the biomass from pressing directly against the loading gate 11. The first retention device 15 therefore releases pressure from the airtight loading gate 11. A first percolate drainage system 24 is provided in the bottom plate 17 between the closed loading gate 11 and the first retention device 15 to collect the percolate that seeps out of the biomass and through the first retention device 15. Thus, the accumulation of percolate between the first retention device 15 and the closed loading gate 11 is prevented. The back end 22 of the bioreactor 10 is constructed similar to the front end 21 and includes a second percolate drainage system 25. FIG. 2 shows an open unloading gate 12 being shut. The second retention device 16 with a construction similar to that of the first retention device 15 is provided in front of the unloading gate 12 and also prevents the biomass from directly pressing against the unloading gate 12.

Figure 3:
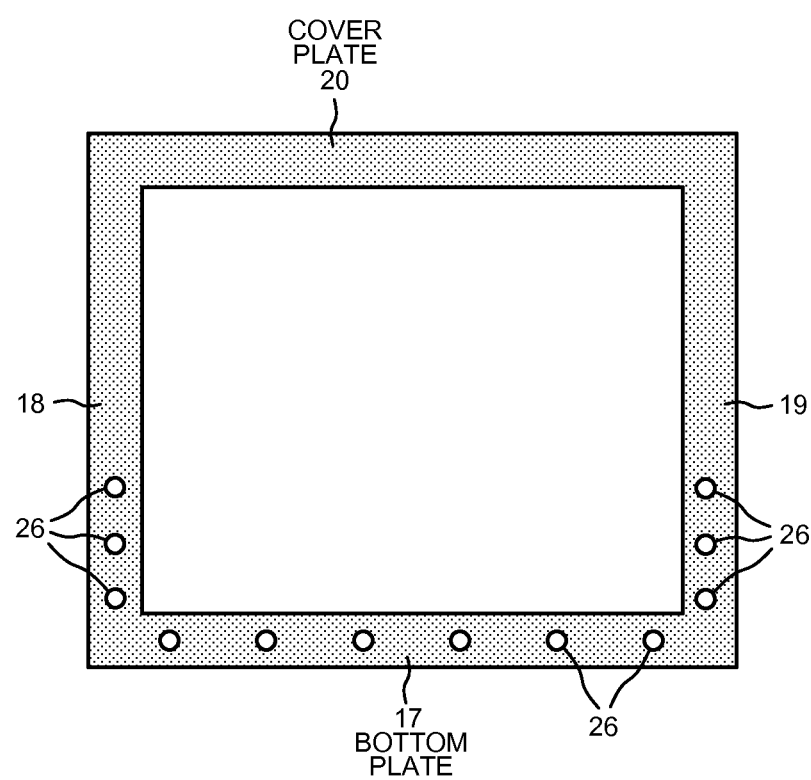
FIG. 3 shows a horizontal cross-sectional view through the bioreactor showing the pipelines of the wall heating and floor heating.

FIG. 3 is a cross-sectional view of reactor container 13. Tubular hoses or pipes 26 are arranged inside the bottom plate 17 and the side walls 18-19. A heating liquid such as hot water is pumped through the pipes 26. The heating pipes 26 enable a thermophilic fermentation process to decontaminate the spent biomass. The heating pipes 26 run along the lengths of the two side walls 18-19 and bottom plate 17. The heating liquid is circulated through the heating pipes 26 in order to maintain a temperature within the reactor container 13 above 55° C.

For additional details regarding the construction of the reactor container 13, see U.S. Pat. No. 8,105,823 dated Jan. 21, 2012, entitled "Biogas Installation for Production of Biogas from Biomass and Methods for Operation of the Biogas Installation," which is incorporated herein by reference. The reactor container of the present invention, however, differs from the reactor container disclosed in U.S. Pat. No. 8,105,823 in that the present invention adds the second gate 12 for unloading, the second retention device 16 and the second percolate drainage system 25. Spent biomass can be pushed out of the reactor container 13 through the unloading gate 12 without being contaminated in the loading zone 14.

U.S. Pat. No. 8,105,823 also provides additional details of a biogas plant that could be constructed from a plurality of reactor fermenters as described herein. Dry fermentation is carried out in each of the reactor containers 13 in a batch process. A constant supply of biogas can be supplied to a cogeneration unit by successively operating several fermenters in the dry fermentation biogas plant. Due to the batch-type operation, individual fermenters must be shut down from time to time. For example, the biogas production must be stopped, the fermented biomass must be removed from the respective fermenter, fresh biomass must be charged into the fermenter, and the biogas production is then resumed. Fresh biomass cannot be added in parallel to fermenters already running in the batch operation, as the quality of the biogas generated in each freshly charged fermenter is poor and would lower the quality of gas provided to the cogeneration unit.

LIST OF REFERENCE NUMERALS 10 bioreactor
11 first gate—loading gate
12 second gate—unloading gate
13 reactor container
14 contaminated loading zone
15 first retention device
16 second retention device
17 bottom plate
18-19 side walls
20 cover plate
21 open front end
22 open back end
23 biogas removal outlet
24 first percolate drainage
25 second percolate drainage
26 tubular heating hoses Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method comprising:
   loading a reactor container with unfermented biomass only through a loading gate, wherein the reactor container includes a bottom plate, a cover plate, two side walls, a front end and a back end, and wherein the biomass rests on the bottom plate;
   sealing the front end in an airtight manner by closing the loading gate;
   generating methane by fermenting the biomass using dry fermentation at a temperature range of 50° C. to 60° C.; and
   unloading spent biomass from the reactor container only through an unloading gate, wherein the unloading gate seals the back end in an airtight manner when the unloading gate is closed, wherein the spent biomass is unloaded from the reactor by pushing unfermented biomass with a loader bucket across the ground, through the front end and onto the bottom plate so as to push the spent biomass across the bottom plate and out the back end.

2. The method of claim 1, wherein the unloading gate covers substantially all of the cross-sectional area of the reactor container at the back end when the unloading gate is closed.

3. The method of claim 1, further comprising:
   composting the spent biomass directly after unloading the spent biomass from the reactor container without first decontaminating the spent biomass after the spent biomass has been unloaded from the reactor container.

4. The method of claim 1, wherein the loading of the reactor container is performed by pushing the unfermented biomass with the loader bucket through the front end and onto the bottom plate that is flush with the ground.

5. The method of claim 1, further comprising:
   repeating the loading, sealing and unloading so as to generate methane in multiple batch operations.

6. The method of claim 1, wherein the reactor container is made of steel-reinforced concrete and has a rectangular cross section.

7. The method of claim 1, wherein the sealing of the front end is performed by hydraulically closing the loading gate.

8. The method of claim 1, wherein the unloading gate is constructed as a flap that articulates from the top of the reactor container.

9. The method of claim 1, further comprising:
preventing the biomass from pressing against the unloading gate by pushing the biomass against a retention device disposed inside the reactor container adjacent to the unloading gate.

10. The method of claim 9, further comprising:
collecting percolate that seeps out of the biomass using a percolate drainage system disposed between the retention device and the closed unloading gate.

11. The method of claim 1, further comprising:
removing a retention device that retains the biomass after opening the unloading gate and before unloading the spent biomass from the reactor container.

12. The method of claim 1, further comprising:
supplying the methane to a cogeneration unit.

\* \* \* \* \*